US008859098B2

(12) United States Patent
Abbey

(10) Patent No.: US 8,859,098 B2
(45) Date of Patent: Oct. 14, 2014

(54) ACRYLIC ADHESION PROMOTERS

(75) Inventor: Kirk J. Abbey, Garner, NC (US)

(73) Assignee: LORD Corporation, Cary, NC (US)

( * ) Notice: Subject to any disclaimer, the term of this patent is extended or adjusted under 35 U.S.C. 154(b) by 252 days.

(21) Appl. No.: 13/475,246

(22) Filed: May 18, 2012

(65) Prior Publication Data

US 2013/0309508 A1 Nov. 21, 2013

(51) Int. Cl.
- *C07F 9/38* (2006.01)
- *B32B 15/06* (2006.01)
- *B32B 27/06* (2006.01)
- *B32B 7/12* (2006.01)
- *B32B 27/40* (2006.01)
- *B32B 27/34* (2006.01)
- *C09J 133/00* (2006.01)

(52) U.S. Cl.
CPC .............. *C07F 9/3808* (2013.01); *B32B 27/40* (2013.01)
USPC ........ 428/411.1; 560/198; 524/853; 524/492; 428/457; 428/465; 428/458; 428/461; 428/462; 428/423.1; 525/455; 156/330; 427/387

(58) Field of Classification Search
CPC ........... B32B 7/10; B32B 7/12; A61K 31/662
USPC ........... 252/8; 8/120; 523/410; 428/410, 420, 428/460
See application file for complete search history.

(56) References Cited

U.S. PATENT DOCUMENTS

| | | | | |
|---|---|---|---|---|
| 2,492,994 A | * | 1/1950 | Denham et al. ............ | 106/284.1 |
| 2,971,948 A | * | 2/1961 | Denk et al. ..................... | 526/278 |
| 2,981,650 A | | 4/1961 | Bader et al. | |
| 3,236,863 A | * | 2/1966 | Smith et al. .................. | 549/216 |
| 3,321,351 A | | 5/1967 | Bader et al. | |
| 3,344,107 A | * | 9/1967 | Miller ........................... | 523/216 |
| 3,456,039 A | * | 7/1969 | Beriger et al. ................. | 558/153 |
| 3,468,984 A | * | 9/1969 | Beriger ......................... | 558/212 |
| 3,538,221 A | * | 11/1970 | Beriger ......................... | 514/147 |
| 3,703,073 A | * | 11/1972 | Goodbar et al. .................... | 57/2 |
| 3,890,407 A | | 6/1975 | Briggs, Jr. et al. | |
| 3,933,427 A | * | 1/1976 | Bohnsack et al. ............. | 422/15 |
| 3,964,921 A | * | 6/1976 | Persinski et al. ............. | 106/719 |
| 3,984,432 A | * | 10/1976 | Piller et al. .................... | 548/119 |
| 4,026,709 A | * | 5/1977 | Piller et al. .................... | 430/552 |
| 4,169,086 A | * | 9/1979 | Nolken ......................... | 524/131 |
| 4,223,115 A | * | 9/1980 | Zalucha et al. ............... | 525/455 |
| 4,293,665 A | | 10/1981 | Zalucha et al. | |
| 4,452,944 A | | 6/1984 | Dawdy | |
| 4,467,071 A | | 8/1984 | Dawdy | |
| 4,483,689 A | * | 11/1984 | Welch ............................. | 8/184 |
| 4,536,546 A | | 8/1985 | Briggs | |
| 4,769,419 A | | 9/1988 | Dawdy | |
| 4,803,250 A | | 2/1989 | Nagasaki et al. | |
| 4,816,086 A | * | 3/1989 | Oleske ......................... | 148/247 |
| 5,091,211 A | * | 2/1992 | Richard ....................... | 427/519 |
| 5,096,962 A | | 3/1992 | Holmes-Farley et al. | |
| 5,206,298 A | | 4/1993 | Kawaguchi | |
| 5,268,404 A | | 12/1993 | Mowrey | |
| 5,359,115 A | * | 10/1994 | Campbell et al. ............. | 558/110 |
| 5,414,102 A | * | 5/1995 | Pohmer et al. .................. | 558/45 |
| 5,420,328 A | * | 5/1995 | Campbell ...................... | 558/110 |
| 5,496,476 A | * | 3/1996 | Tang et al. ......................... | 8/120 |
| 5,608,098 A | * | 3/1997 | Peyman et al. ............... | 558/145 |
| 5,641,834 A | * | 6/1997 | Abbey et al. ..................... | 525/77 |
| 5,710,235 A | | 1/1998 | Abbey et al. | |
| 5,859,160 A | | 1/1999 | Righettini et al. | |
| 5,932,638 A | | 8/1999 | Righettini et al. | |
| 5,976,772 A | * | 11/1999 | Hubsch et al. ................ | 430/393 |
| 6,184,013 B1 | * | 2/2001 | Landry et al. ............. | 435/188.5 |
| 6,221,955 B1 | * | 4/2001 | Mequanint et al. ........... | 524/591 |
| 6,225,408 B1 | | 5/2001 | Huang et al. | |
| 6,255,476 B1 | * | 7/2001 | Vinayak et al. ............. | 536/25.32 |
| 6,316,610 B2 | * | 11/2001 | Lee et al. ...................... | 536/23.1 |
| 6,326,453 B2 | | 12/2001 | Asami et al. | |
| 6,350,839 B2 | * | 2/2002 | Moszner et al. .............. | 526/278 |
| 6,559,257 B2 | | 5/2003 | Quarmby | |
| 6,630,555 B2 | | 10/2003 | Kendall et al. | |
| 6,645,631 B2 | | 11/2003 | Gan et al. | |
| 6,646,076 B1 | | 11/2003 | Kendall et al. | |
| 6,660,805 B1 | | 12/2003 | Righettini et al. | |
| 6,710,149 B2 | * | 3/2004 | Moszner et al. .............. | 526/278 |
| 6,835,827 B2 | * | 12/2004 | Vinayak et al. .............. | 536/25.3 |
| 7,009,009 B1 | | 3/2006 | Crane et al. | |
| 7,019,075 B2 | | 3/2006 | Righettini et al. | |
| 7,265,379 B2 | * | 9/2007 | Sandberg et al. .............. | 257/40 |
| 7,344,895 B2 | * | 3/2008 | Kohler et al. ................. | 436/523 |

(Continued)

FOREIGN PATENT DOCUMENTS

| JP | 6-192029 | * | 1/1994 |
|---|---|---|---|
| JP | 7-331082 | * | 1/1995 |

OTHER PUBLICATIONS

Self-assembling adhesion promoters for corrosion resistant metal polymer interfaces, Maege et al., Progress in Organic Coatings 34 (1998) 1-12.*

Structure and stability of adhesion promoting aminopropyl phosphonate layers at polymer aluminum oxide interfaces, Wapner et al., International Journal of Adhesion and Adhesives 28, (2007) 59-70.*

Comparative study on stabilizing effect of 2-phosphonobutane-1,2,4-tricarboxylic acid and citric acid for alumina suspensions, Yangqiao et al., Colloids and Surface (2001) 187-195.*

(Continued)

*Primary Examiner* — Callie Shosho
*Assistant Examiner* — Michael B Nelson
(74) *Attorney, Agent, or Firm* — Todd W. Galinski

(57) ABSTRACT

Acrylic adhesion promoters having an improved property such as cohesive failure are produced from a monocyclic anhydride of phosphonic acid containing multiple carboxylic acids that is subsequently reacted with a hydroxyalkyl methacrylate. The adhesion promoters are useful in bonding to metal substrates including oily metal substrates.

22 Claims, No Drawings

(56) References Cited

U.S. PATENT DOCUMENTS

| | | | |
|---|---|---|---|
| 7,494,540 B2* | 2/2009 | Wu et al. | 106/287.11 |
| 7,514,419 B2* | 4/2009 | Erion et al. | 514/140 |
| 7,547,745 B2 | 6/2009 | Valette | |
| 7,549,425 B2 | 6/2009 | Koga et al. | |
| 7,595,425 B2 | 9/2009 | Estevez et al. | |
| 7,622,516 B1 | 11/2009 | Starkey | |
| 7,662,879 B2* | 2/2010 | Bhandarkar et al. | 524/430 |
| 7,829,552 B2* | 11/2010 | Erion et al. | 514/140 |
| 7,851,515 B2* | 12/2010 | Salz et al. | 523/115 |
| 7,910,024 B2 | 3/2011 | Stapp et al. | |
| 8,183,306 B2* | 5/2012 | Kohro et al. | 523/116 |
| 8,530,212 B2* | 9/2013 | Moloney et al. | 435/180 |
| 8,586,208 B2* | 11/2013 | Sharma et al. | 428/690 |
| 8,642,165 B2* | 2/2014 | Suzuki et al. | 428/220 |
| 2001/0014735 A1* | 8/2001 | Lee et al. | 536/23.1 |
| 2001/0044513 A1* | 11/2001 | Moszner et al. | 526/278 |
| 2001/0051701 A1* | 12/2001 | Quarmby | 526/270 |
| 2002/0016384 A1* | 2/2002 | Moszner et al. | 523/115 |
| 2002/0107146 A1* | 8/2002 | Loccufier et al. | 503/212 |
| 2003/0098441 A1* | 5/2003 | Verma | 252/194 |
| 2004/0229990 A1* | 11/2004 | Righettini et al. | 524/445 |
| 2004/0249028 A1* | 12/2004 | Fujimura et al. | 524/115 |
| 2005/0191660 A1* | 9/2005 | Vinayak et al. | 435/6 |
| 2005/0215513 A1* | 9/2005 | Boojamra et al. | 514/47 |
| 2005/0227947 A1* | 10/2005 | Chen et al. | 514/79 |
| 2006/0018948 A1* | 1/2006 | Guire et al. | 424/426 |
| 2006/0130701 A1* | 6/2006 | Salz et al. | 106/35 |
| 2007/0027114 A1* | 2/2007 | Fardis et al. | 514/81 |
| 2008/0070868 A1* | 3/2008 | Dang et al. | 514/92 |
| 2009/0028925 A1* | 1/2009 | Erion et al. | 424/443 |
| 2009/0156558 A1* | 6/2009 | Fardis et al. | 514/81 |
| 2009/0299006 A1* | 12/2009 | Shinno et al. | 524/807 |
| 2010/0010115 A1* | 1/2010 | Kohro et al. | 523/116 |
| 2010/0081634 A1* | 4/2010 | Erion et al. | 514/89 |
| 2010/0104842 A1* | 4/2010 | Suzuki et al. | 428/220 |
| 2010/0216911 A1* | 8/2010 | Doshi et al. | 523/200 |
| 2011/0114936 A1* | 5/2011 | Akimoto et al. | 257/40 |
| 2011/0130479 A1 | 6/2011 | Kramer et al. | |
| 2011/0288053 A1* | 11/2011 | Boojamra et al. | 514/80 |
| 2012/0114974 A1* | 5/2012 | Hotchkiss et al. | 428/702 |
| 2012/0115108 A1* | 5/2012 | Blomker et al. | 433/217.1 |
| 2012/0214769 A1* | 8/2012 | Gomez-Galeno et al. | 514/92 |
| 2013/0034743 A1* | 2/2013 | Bannai et al. | 428/624 |
| 2013/0296195 A1* | 11/2013 | Gray et al. | 506/18 |
| 2013/0316969 A1* | 11/2013 | Boojamra et al. | 514/48 |

OTHER PUBLICATIONS 2-acyloxyethylphosphonate analogues of Prenyl Pyrophosphates: synthesis and biological characterization, Cermak et al., Bioorganic Medicinal Chemistry 8 (2000) 2729-2737.*

STN search results, searched on Feb. 25, 2014.*

* cited by examiner

ACRYLIC ADHESION PROMOTERS

FIELD OF THE INVENTION

The present invention relates to adhesion promoters for acrylic adhesives that are produced by dehydrating a phosphonic acid containing multiple carboxylic acid groups to produce an anhydride containing phosphonic acid that can be subsequently reacted with a hydroxyalkyl methacrylate. These adhesion promoters generally have good cohesive failure properties and can bond to oily metal surfaces.

BACKGROUND OF THE INVENTION

Heretofore, phosphate-based acrylic adhesive promoters have been utilized to vastly improve the adhesion of methacrylate structural adhesives to metals including metals coated with mill oils from stamping and cutting operations. Phosphonic acid based adhesion promoters have not been as readily available. There is a desire for improved corrosion resistance in adhesively bonded metal assemblies. The phosphate ester linkage is suspected as being a weak link in the adhesives using phosphate-based adhesion promoters.

U.S. Pat. No. 4,223,115 relates to structural adhesive systems for metal-bonding applications comprising a solution or dispersion of a polymeric material in a monomer copolymerizable therewith having incorporated therein certain phosphorus-containing compounds that are characterized by an unexpected ability of providing strong adhesion to untreated metal surfaces without adversely affecting adhesive performance, including resistance to deleterious environments. The environmental resistance of the described adhesives can be further improved by the addition of one or more polybasic lead salts, metal molybdates and metal phosphates.

U.S. Pat. No. 6,326,453 relates to a novalak-type phenol resin reportedly with less unreacted phenol and a narrow molecular weight distribution that is reportedly produced in high yield by reaction of a phenol with an aldehyde using an organophosphoric acid as a catalyst, while keeping a water concentration of reaction system at not more than 30% by weight and a reaction temperature at 110° C. to 200° C.

U.S. Pat. No. 7,910,024 relates to compositions and methods for inhibiting corrosion of corrodible metals present in contact with water in cooling water and other water storage systems. The compositions include concentrated stannous salts and agents to solubilize such salts.

SUMMARY OF THE INVENTION

The present invention relates to the dehydration of phosphonic acids that contain multiple carboxylic groups to form mono-cyclic anhydride compounds, or if the phosphonic acid contains more than two carboxylic acid groups, the anhydride compound can be reacted with an alcohol and subsequently reacted with an alkyl anhydride to form a useful monocarboxylated phosphonic acid anhydride. Upon further reaction with a hydroxyalkylmethacrylate, an acrylic adhesion promoter containing phosphonic acid is produced.

The present invention also relates to a carboxylic acid containing phosphonic acid adhesion promoter comprising a compound of the formula:

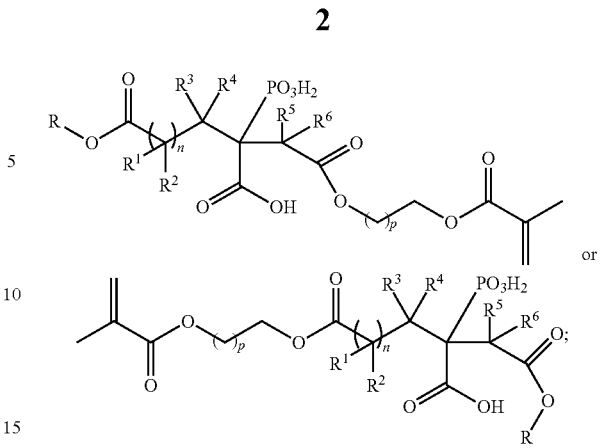

wherein R is H, or an alkyl having from 1 to about 18 carbon atoms, $R^1$, independently, is H, or from 1 to about 6 carbon atoms,
$R^2$, independently, is H, or from 1 to about 6 carbon atoms,
$R^3$, independently, is H, or from 1 to about 6 carbon atoms,
$R^4$, independently, is H, or from 1 to about 6 carbon atoms
$R^5$, independently, is H, or from 1 to about 6 carbon atoms,
and
$R^6$, independently, is H, or from 1 to about 6 carbon atoms
and wherein n, independently, is 0 or 1 and p, independently, is from about 1 to about 35.

DETAILED DESCRIPTION OF THE INVENTION

The phosphonic acids utilized in the present invention can contain from 1 to 4 carboxylic acid groups and preferably are multiple carboxylated compounds having 2 to about 3 COOH groups and contain a total of from about 4 to about 25 carbon atoms and desirably from about 5 to about 10 or about 15 carbon atoms. A preferred phosphonic acid contains 4 non-acid carbon atoms and 3 COOH groups. Thus, 2-phosphonobutane-1,2,4-tricarboxylic acid (PBTA) is preferred in one embodiment and is generally available as an aqueous solution. Desirably such compounds are sequentially dehydrated to produce a phosphonic acid having at least one anhydride group thereon.

Dehydration can be achieved by azeotropic distillation in the presence of an inert atmosphere such as nitrogen, argon, or $CO_2$, an azeotropic agent such as various hydrocarbons having from about 6 to about 10 carbon atoms, e.g. xylene, cyclohexane, toluene, or other non-reactive material known to azeotrope with water and a solvent.

The solvent must be a compound that will dissolve polar materials such as PBTA and other carboxylic acid functionalized phosphonic acids and the anhydride products produced but does not react with the acids or anhydrides formed during the dehydration. Suitable solvents include sulfolane, i.e. tetrahydrothiophene-1,1-dioxide, also known as tetramethylene sulfone, dimethylsulfone, ethylmethylsulfone; dialkyl sulfones whether cyclic or acyclic having a total of from about 2 to about 12 carbon atoms, and sterically congested ketones such as 2,6-dimethyl cyclohexanone and diisopropyl ketone.

The above mixture is heated in a reactor equipped with a Dean-Stark trap, condenser, stirrer, and the like. The reactor is heated for a few hours until no trace of water is left and most of the azeotropic agent has been removed. Suitable heating temperatures generally are that of the boiling point of the azeotropic solution or mixture. The maximum temperature reached using PBTA should not exceed 170° C. and preferably not above 160° C. For PBTA, the above dehydration route forms a monocyclic anhydride of PBTA, see Reaction Scheme I, Formulas 1a and 1b, and General Reaction Scheme III, Formulas G1a and G1b. Suitable uses of the monocyclic anhydride of PBTA include adhesion promoters for acrylic adhesives, and as a curative for epoxy resins.

The monocyclic anhydride phosphonic acid, e.g. Formulas 1a and 1b, and G1a and G1b, can be reacted with one or more alcohols to form a monoalkylcarboxylated phosphonic acid, see Reaction Scheme II, Formulas 3a and 3b, and General Reaction Scheme III, Formulas G3a and G3b. That is, a molar excess of the one or more anhydrous alkyl alcohols having from 1 to about 18 and desirably from about 1 to about 4 atoms, or preferably 2 carbon atoms, can then be added to the anhydride containing phosphonic acid at such a rate as to prevent undesirably rapid reflux, generally over 30 minutes (depending upon the cooling capabilities of the reactor). The amount of the one or more alcohols is generally from about 1.0 to about 1.2 moles and desirably from about 1.05 to about 1.1 moles based on the molar equivalents of anhydride present. Once all of the alcohol has been added, heating is resumed to maintain a temperature at or below, e.g. about 5° C., or about 10° C., or about 15° C., the reflux temperature of the alcohol br about 30 to about 90 minutes to ensure complete reaction of the anhydride. This step results in a carboxylic acid functional phosphonic acid compound containing one less carboxylic acid group than the original phosphonic acid, see Formulas 3a and 3b as well as G3a and G3b. The added alkyl ester moiety greatly improves the solubility of the phosphonic acid in less polar media.

For initial phosphonic acid materials containing three carboxylic acid groups, the newly formed ester containing species, e.g. Formulas 3a and 3b, and G3a and G3b, can be dehydrated a second time. While thermal, azeotropic dehydration can be used to form a second anhydride functional group on the phosphonic acid, the reaction is partially accompanied by a reversion to the initial anhydride species with loss of alcohol from the above formed ester. Alternatively, a mild dehydration route uses a lower alkyl acyclic anhydride having from 4 to about 8 carbon atoms and preferably 4 carbon atoms, i.e. acetic anhydride. Other mild dehydrating agents that can be used include a carbodiimide having a total of from about 5 to about 15 carbon atoms such as cyclohexyl carbodiimide, or 1,1'-oxalyldiimidazole, lower alkyl acid chlorides having from about 2 to about 6 carbon atoms such as acetyl chloride and oxalyl dichloride, or thionyl chloride, or an ethoxyacetylene such as (trimethylsilyl)ethoxyacetylene. The reaction temperature is generally from about 80° C. b about 130° C. and preferably from about 90° C. to about 120° C. when an anhydride is used Milder conditions are possible with some of the other dehydrating agents. The produced monocarboxylated phosphonic acid anhydride, see Reaction Formation Schemes II and III, is purified of excess dehydrating agent and its by-products by stripping them from the reaction mixture. The stripping step can vary depending upon the equipment used. Advantageously, this can be done by a wiped film evaporator or vented extruder to minimize the contact time under heating. Reduced pressure is preferably desired to allow the lowest possible temperature to be used. Pressures less than about 10 torr and preferably down to about 1 torr are desired. The temperature should not be allowed to exceed about 150° C. irrespective of the pressure obtainable.

If azeotropic dehydration is used with respect to the Formula 3 compound, the same azeotropic agents and solvents as used in the production of the monocyclic anhydride of Formulas 1a and 1b, and G1a and G1b noted above, can be used again but it need not be the exact same agent. During the second dehydration reaction, the reaction temperature is up to the boiling point of the azeotropic solution, e.g. a maximum temperature of from about 145° C. to about 155° C. This maximum temperature will occur during the removal of azeotropic agent. Reduced pressure can be used with about 50 torr or preferably about 10 torr being ultimately achieved. A monocarboxylated phosphonic acid anhydride is produced, see Formulas 4a and 4b, and G4a and G4b.

When PBTA is utilized, the second anhydride obtained by either the mild dehydration route or the second thermal azeotropic route occurs at a site different from the first anhydride and the structure of the phosphonic acid compound can either be a 1,2 or 2,4 structure, see Formulas 4a and 4b, and G4a and G4b. The number 2 carbon atom has a carboxylic acid group and also a phosphonic acid group attached thereto. As noted, the first anhydride group as shown in Formulas 1a and 1b, and G1a and G1b have been reacted to form an ester group as shown in Formulas 3a and 3b, and G3a and G3b. When the thermal azeotropic route is utilized, but not preferred due to poor solubility, to form a second anhydride, part of the reaction is a reversion of the Formulas 3a and 3b, and G3a and G3b compounds with loss of the alcohol group to form products of Formulas 1a and 1b, and G1a and G1b. Thus, the end products are a mixture of the compounds of Formulas 1a and 1b, and G1a and G1b with the compounds of Formulas 4a and 4b, and G4a and G4b.

Regardless of whether the anhydride route or the second azeotropic route is utilized, a hydroxyalkyl methacrylate is added to a reaction vessel containing the monocarboxylated phosphonic acid anhydride such as HEMA, see Formulas 4a and 4b, and G4a and G4b, and 5a and 5b, and G5a and G5b in an amount of from about 0.9 to about 1.1 moles and desirably from about 1.00 to about 1.05 moles per mole of initial tricarboxylic acid phosphonic acid to form a methacrylate adduct. The alkyl ester group of the methacrylate compound generally has from about 2 to about 36 carbon atoms and desirably from about 2 to about 10 carbon atoms and with 2 carbon atoms, i.e. ethylene being most highly preferred. This reaction desirably occurs in air at temperatures of from about ambient (e.g. 20° C.) to shout 100° C., desirably from about 40° C. to about 70° C., and preferably from about 45° C. to about 65° C. for about 60 minutes to about 500 minutes and desirably for about 90 minutes to about 180 minutes. An optional addition of 20-200 ppm of a suitable inhibitor may also be used in this stage to prevent possible polymerization. The end product or compound, see Formulas 5a and 5b, and G5a and G5b, is an adhesion promoter containing phosphonic acid that is useful in various types of adhesives such as acrylic adhesives to bond metallic substrates, such as steel, stainless steel, aluminum, galvanized steel, phosphated steel, copper, brass, bronze, lead, nickel, zinc, Monel steel, and the like, including crossbonding of metallic substrates, to non-metallic substrates such as rubbers, plastics, and the like and thus form various laminated articles. Examples of rubbers include natural rubber, polychloroprene rubber, styrenebutadiene rubber, nitrile rullber, ethylene/-propolyene copolymer rubber (EPM); ethylene/-propylene/diene terpolymer rubber (EPDM); butyl rubber, polyurethane rubber, parel type elastomers, and the like. Examples of plastics include polyamides, polyesters, aramides, e.g., Kevlar, a trademark of E.I. de Pont de Nemours Co., (Inc.), of Wilmington, Del., polyurethanes, and the like.

The above various reactions are generally set forth with regard to specific reactants in the following Reaction Scheme I and Reaction Scheme II utilizing PBTA. The adhesion promoters containing phosphonic acid have been found to have very good adhesion properties even with respect to oily metal surfaces as set forth hereinbelow.

REACTION SCHEME I

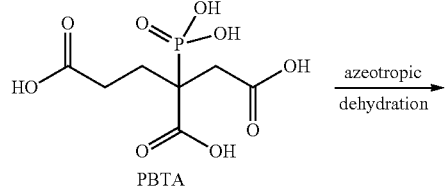

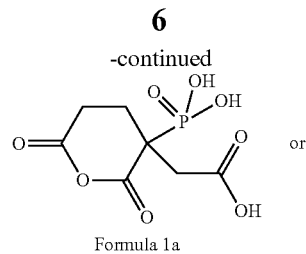

Formula 1a

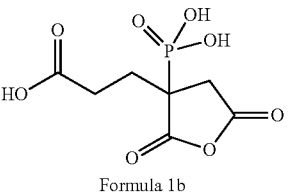

Formula 1b

REACTION SCHEME II

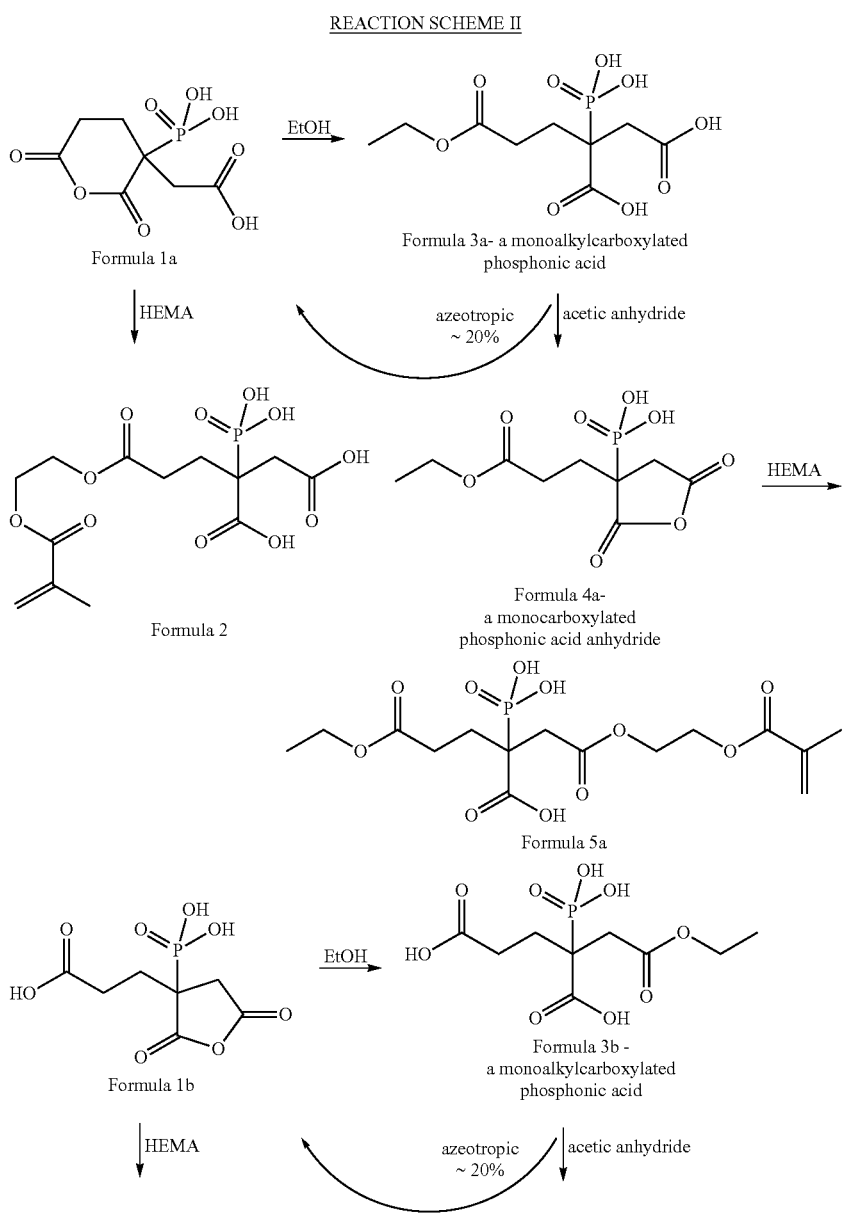

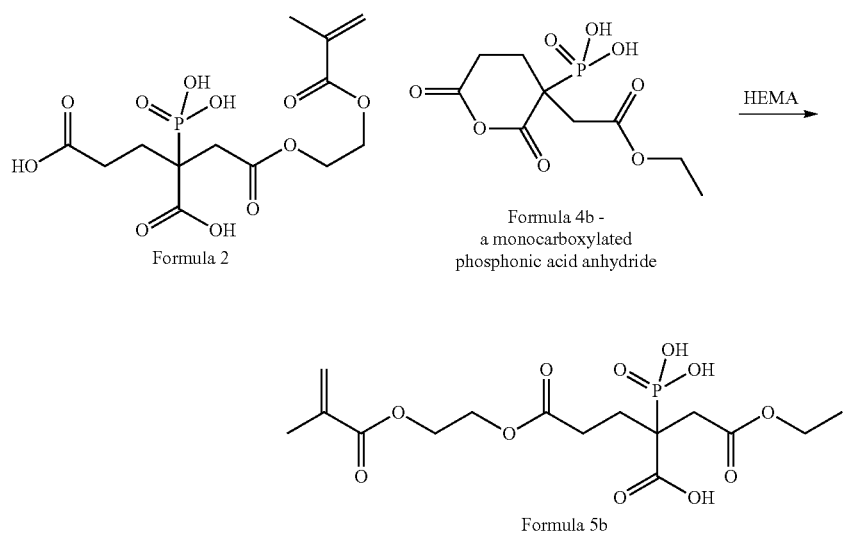

The above Schemes I and II relate to specific carboxylated phosphonic acids and to specific reactions therewith with specific compounds such as acetic anhydride, and HEMA, Scheme III relates to a general or generic representation of various reactions of the anhydride formed by azeotropic dehydration with various alcohols, and subsequently with various hydroxyalkymethacrylates.

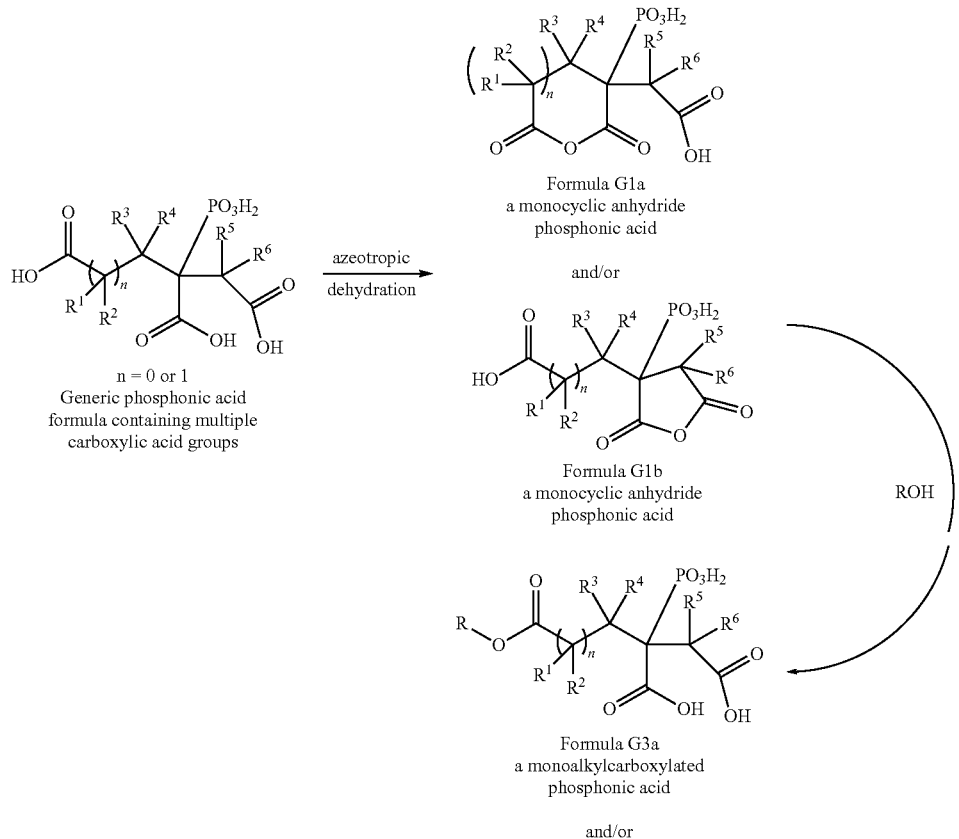

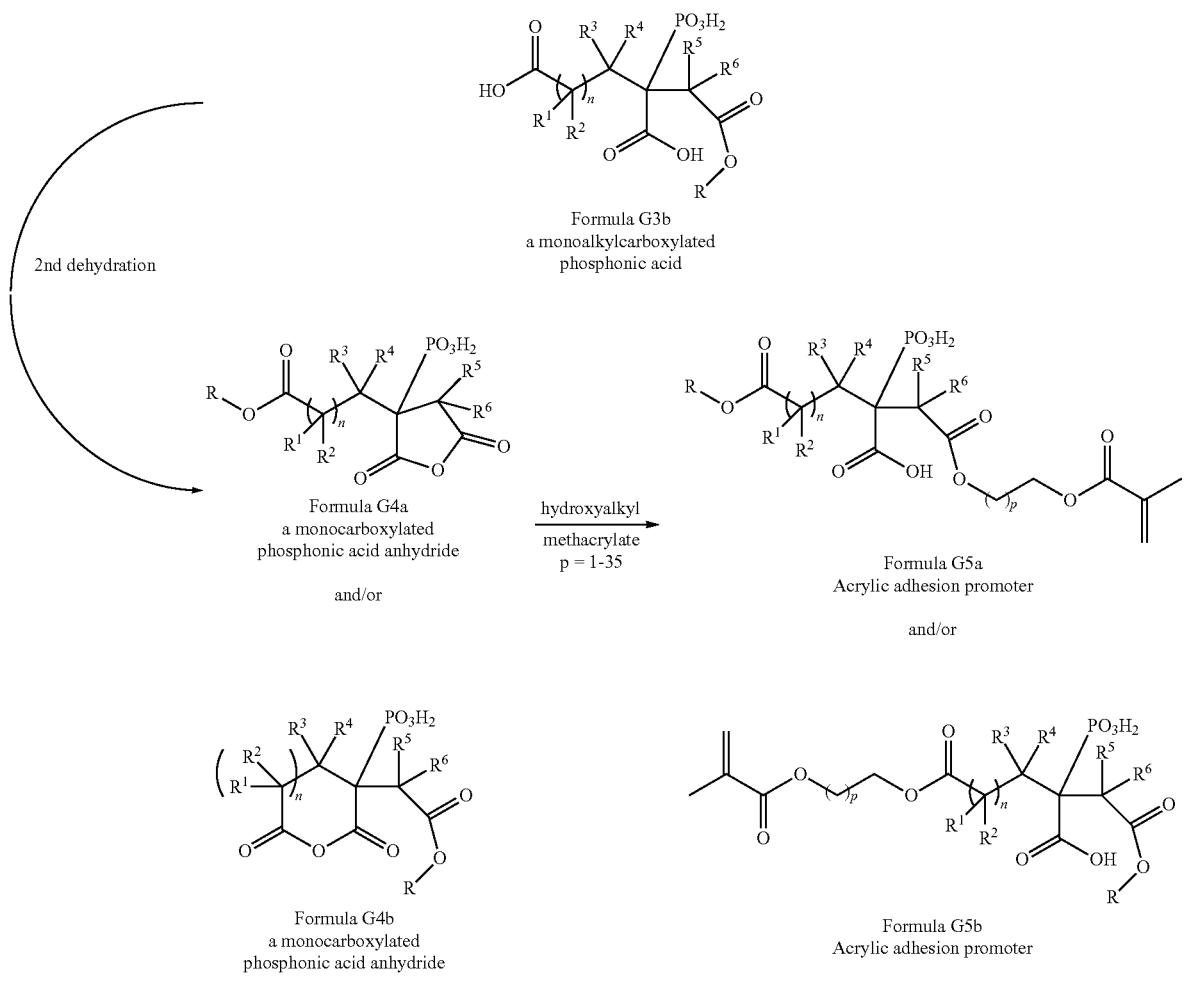

With regard to reaction Scheme III, R is hydrogen or an alkyl having from 1 to about 18 carbon atoms, desirably from about 1 to about 4, and preferably 2 carbon atoms. $R^1$, $R^2$, $R^3$, $R^4$, $R^5$, and $R^6$, independently, is H, or an alkyl having from 1 to about 6 carbon atoms, or is H, or from 1 to about 2 carbon atoms, or preferably is H or methyl, i.e. one carbon atom. n, independently, is 0 or 1, and p, independently, is from about 1 to about 35, desirably from about 1 to about 10, and preferably from about 1 to about 5.

In lieu of tricarboxylated phosphonic acids, various dicarboxylated phosphonic acids as set forth in Reaction Scheme IV, can be dehydrated to form an anhydride in the manner as set forth hereinabove and subsequently reacted with a hydroxyalkyl methacrylate to yield the acrylic adhesive promoter containing phosphonic acid as set forth in the right column of Reaction Scheme IV. The dehydration step to produce the various phosphonic acid anhydride compounds is generally the same as set forth hereinabove such as to produce Formulas 1a and 1b and are fully incorporated by reference. By way of a brief summary, azeotropic distillation is utilized in an inert atmosphere, for example nitrogen, utilizing various above-noted azeotropic agents such as xylene and a suitable solvent such as sulfolane and are heated in a reactor that can be equipped with the Dean-Stark trap, condenser, stirrer, and the like. The maximum reaction temperature is the boiling point of the azeotropic solution that varys with the solvent and azeotropical agent, and hence can be up to about 160° C. or about 170° C. and the reaction is continued until notrace of water is left and most of the azeotropic agent has been removed. The intermediate anhydride is shown in Reaction Scheme IV that is subsequently reacted with a hydroxyalkyl methacrylate compound, e.g. a type noted hereinabove and fully incorporated by reference, such as HEMA in an amount of from about 0.9 to about 1.10 and desirably from about 1.00 to about 1.05 moles per mole of equivalent anhydride at a reaction temperature of from about 40° C. to about 70° C., desirably from about 45° C. to about 65° C. to yield the acrylic adhesion promoter containing phosphonic acid. With respect to the dicarboxylated phosphonic acids of Reaction Scheme IV, the first four are known and the last one, i.e. bottom compound, can be made from the dimer of methyl methacrylate, i.e. dimethyl 4,4-dimethyl-2-methyleneglutarate, in a manner as set forth in U.S. Pat. No. 4,547,323, hereby fully incorporated by reference.

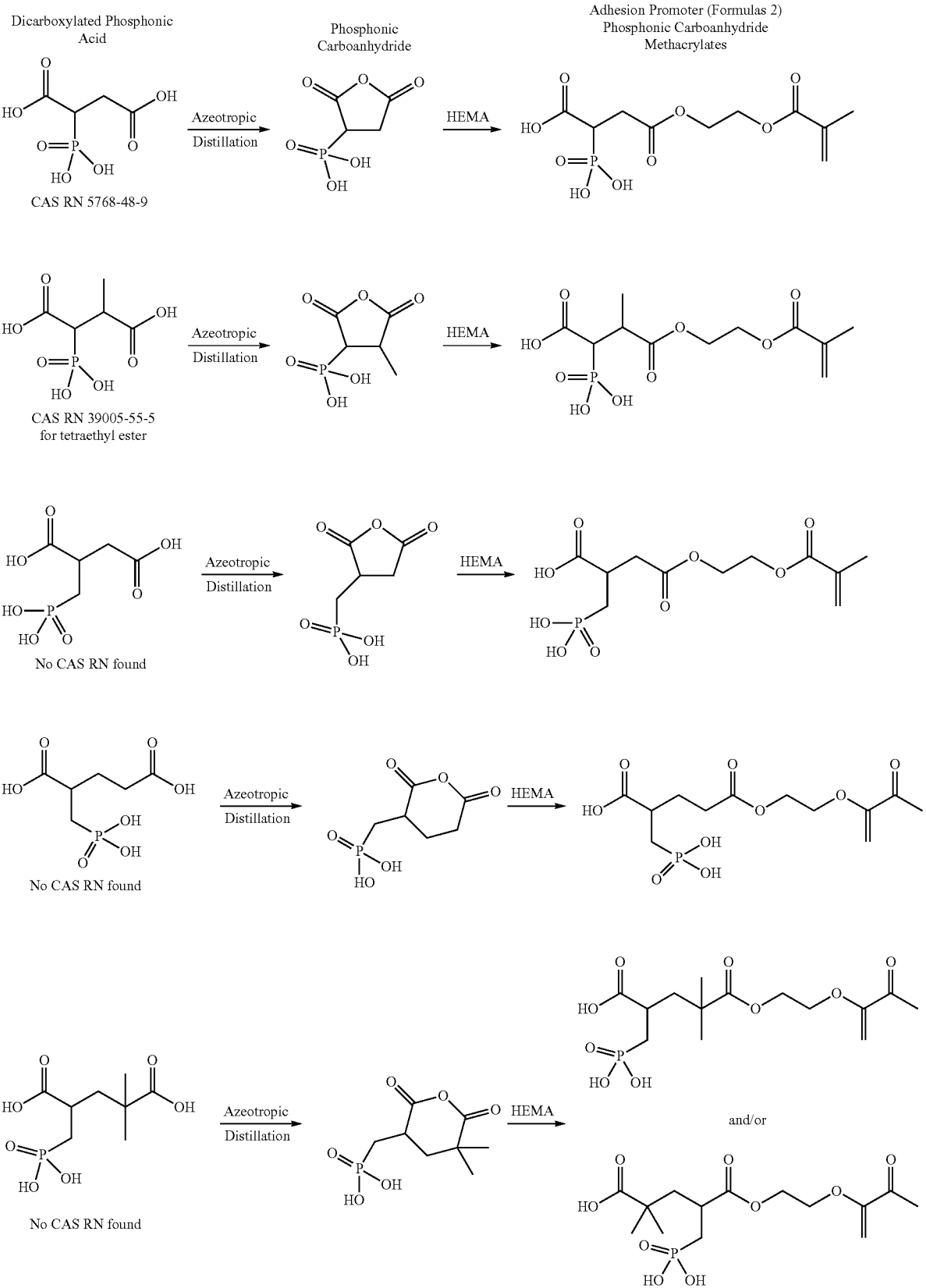
REACTION SCHEME IV

Optionally, hydroxylalkyl acrylates can be utilized in the present invention. When utilized, they can be utilized in conventional amounts, or if not desired, they can be utilized in combination with the methacrylate derivative to give the same overall concentration of active adhesion promoter as determined by optimizing the adhesive formulation.

The invention will be better understood by reference to the following examples which serve to illustrate, but not to limit the present invention.

Detailed Synthesis of Example A

Dehydration of PBTA to Yield a Monocyclic Anhydride of Phosphonic Acid (e.g. Scheme 1)

A four-neck round-bottomed flask (RBF) had a thermocouple well inserted through a combination adapter including $N_2$ inlet, a Dean-Stark trap and condenser, an overhead stirrer with a glass stir rod and Teflon paddle, and a glass stopper in its remaining necks. The PBTA (162.122 g, 0.600 moles) was poured into the RBF with sulfolane (32.369 g, 0.269 moles) and o-xylene (68.97 g, 0.650 moles). The nitrogen flow, the overhead stirrer, the cold water for the condenser, and the mantle were turned on. Heating and stirring of the reaction continued for 222 minutes until there was no trace of water in the reaction and most of the o-xylene was removed (maximum temperature 154° C.).

Formation of a Monocarboxylated Phosphonic Acid, (e.g. Scheme II, Formulas 3a and 3b)

Separately, ethanol (~100 mL) and cyclohexane (~100 mL) were added to a separate single-necked RBF with a Dean-Stark trap and a condenser and refluxed to dry the ethanol (~150 minutes). Dried ethanol (17.587 g, 0.382 moles) was added to the dehydrated PBTA (DPBTA) and stirred for 102 minutes at ~90° C.

Formation of a Monocarboxylated Phosphonic Acid Anydride, (e.g. Scheme II, Formulas 4a and 4b)

Acetic anhydride (51.064 g, 0.500 moles) was subsequently added to the reaction mixture and the acetic acid and remaining acetic anhydride were stripped for 309 minutes under a reduced pressure of ~105 torr until the internal temperature reached ~135° C.

Formation of an Alkyl Methacrylated Phosphonic Acid Adhesive (e.g. Scheme II, Formulas 5a and 5b)

2-Hydroxyethyl methacrylate (HEMA) (41.14 g, 0.316 moles) was added to the reaction through an addition funnel. The reaction atmosphere was changed to air. After the addition was complete, the reaction proceeded for 444 minutes at −50° C.

Detailed Synthesis of Example B

Dehydration of PBTA to Yield a Monocyclic Anhydride of Phosphonic Acid (e.g. Scheme 1, Formulas 1a and 1b)

A four-neck round-bottomed flask (RBF) had a thermocouple well inserted through a combination adapter including N2 inlet, a Dean-Stark trap and condenser, an overhead stirrer with a glass stir rod and Teflon paddle, and a glass stopper put in its remaining necks. The PBTA (152.58 g, 0.565 moles) was poured into the RBF with sulfolane (30.656 g, 0.255 moles) and o-xylene (45.98 g, 0.433 moles). The nitrogen flow, the overhead stirrer, the cold water for the condenser, and the mantle were turned on. Heating and stirring of the reaction continued for 345 minutes until there was no trace of water in the reaction and most of the o-xylene was removed (maximum temperature 154.3).

Formation of a Monocarboxylated Phosphonic Acid, (e.g. Scheme II, Formulas 3a and 3b)

Separately, ethanol (~50 mL) and cyclohexane (~51 mL) were added to the separate single-necked RBF with a Dean-Stark trap and a condenser and the mixture was refluxed with azeotropic removal of water to dry the ethanol (95 minutes). Dried ethanol (13.801 g, 0.300 moles) was added to the dehydrated PBTA (DPBTA) and stirred for 149 minutes and reached a maximum temperature of 89.1° C.

Second Dehydration Reaction

An additional amount of o-xylene (45.98 g, 0.433 moles) was added to the PBTA-ethyl ester for another dehydration reaction. The dehydration reaction was continued for 183 minutes and reached a maximum temperature of 157.6° C.

Formation of an Alkyl Methacrylated Phosphonic Acid Adhesive (e.g. Formulas 5)

2-Hydroxyethyl methacrylate (HEMA) (38.66 g, 0.297 moles) was added to the reaction through an addition funnel. The reaction atmosphere was changed to air. The total addition process continued for 194 minutes and reached a maximum temperature of 74.0° C.

The above phosphonic acid adhesion promoters were then tested as follows:

Example Formulations

Acrylic adhesive formulations were made with the phosphonic adhesion promoter of Example A and compared to identical adhesives without any adhesion promoter and to LORD HEMA-phosphate adhesion promoter, see Lord Corporation U.S. Pat. No. 4,223,115. Clean unpolished hot-dipped galvanized steel was bonded as T-peel specimens and cured for 16 hours at room temperature. The five assembled coupons made with each formulation were pulled apart on an Instron tensile test machine equipped with a 50KN load cell at two inches per minute yielding the values summarized in Table 1.

TABLE 1

| Formulation | Average Maximum Load (N) | Average LD/W (N/m) | Failure Mode* |
|---|---|---|---|
| Control (no adhesion promoter) | 240 ± 40 (5) | 800 ± 400 (4) | 100 ± 0% (5) ADH |
| Control (LORD HEMA-phosphate) | 390 ± 40 (5) | 9,600 ± 200 (5) | 79 ± 7% (5) COH/TLC |
| PBTA-based (Example A) | 370 ± 20 (5) | 10,200 ± 200 (5) | 100 ± 0% (5) COH |

*ADH = adhesive; COH = cohesive; TLC = thin layer cohesive

As apparent from Table 1, the adhesion promoters of the present invention for acrylic adhesives, i.e. Example A, gave a much higher cohesive failure mode than either of the Controls.

Table 2 lists the ingredients used in the model adhesive. They were combined in a disposable plastic beaker in the order listed.

TABLE 2

| Components | Wt (g) | Wt. (%) |
|---|---|---|
| 80/20 THF-MA/Europrene Sol T-193A (manufactured by Polimeri Europa is a SIS (Styrene Isoprene Styrene Block Copolymer) plastic material) | 21.00 | 87.39 |
| DIIPT (N,N-diisopropanol-p-toluidine, the reductant portion of the redox initiator system) | 0.200 | 0.83 |
| N,N-Dimethylaniline | 0.150 | 0.62 |
| GMA-CTB adduct (Adduct of glycidyl methacrylate and carboxylic acid terminated butadiene rubber. See U.S. Pat. No. 4,769,419) | 1.500 | 6.24 |

TABLE 2-continued

| Components | Wt (g) | Wt. (%) |
|---|---|---|
| Adhesion promoter* | 0.480* | 2.00 |
| Cab-O-Sil HS-5 | 0.500 | 2.08 |
| 97% Benzoyl peroxide | 0.200 | 0.83 |
| Total | 24.03 | 100.00 |

*Adhesion promoter, i.e. Example A, or Lord HEMA phosphate, see U.S. Pat. No. 4,223, 115, or Control made without any adhesion promoter but used indicated amount of 80/20 THF-MA/Europrene.

Acrylic Adhesion Compositions

Suitable acrylic adhesion compositions are generally known to the art and to the literature and typically include one or more free radical polymerizable monomers, at least one rubber toughener, optionally a redox catalyst, optionally fillers, coloring agents, and one or more speed control agents to control the open time (the time between application of the mixed adhesive and the time when bonding performance is compromised because of advancing cure), and oxygen barriers, e.g. waxes.

The carboxyl acid containing phosphonic acid adhesion promoters of the present invention can be utilized in numerous acrylic-type adhesive compositions. The following represent some examples of useful acrylic adhesion compositions as set forth in the following U.S. patents which are hereby fully incorporated by reference.

U.S. Pat. No. 6,630,555 includes free radical polymerizable components that can be monofunctional and/or polyfunctional including a combination of monofunctional and polyfunctional monomers, oligomers and polymers, including mixtures thereof. There are widely available monofunctional acrylate and methacrylate esters, and the substituted versions such as hydroxy, amide, cyano, chloro, and silane substituted derivatives. Specific examples include methyl acrylate, methyl methacrylate, ethyl acrylate, ethyl methacrylate, butyl methacrylate, butyl acrylate, cyclohexyl acrylate, hexyl acrylate, 2-ethylhexyl acrylate, isobornyl methacrylate, hydroxyethyl methacrylate, hydroxypropyl acrylate, hydroxypropyl methacrylate, n-octyl acrylate, cyclohexyl methacrylate, hexyl methacrylate, 2-ethylhexyl methacrylate, decyl methacrylate, dodecyl methacrylate, lauryl acrylate, tert-butyl methacrylate, acrylamide, N-methyl acrylamide, diacetone acrylamide, N-tert-butyl acrylamide, N-tert-octyl acrylamide, N-butoxyacrylamide, gamma-methacryloxypropyl trimethoxysilane, dicyclopentadienyloxyethyl methacrylate, 2-cyanoethyl acrylate, 3-cyanopropyl acrylate, tetrahydrofurfuryl methacrylate, tetrahydrofurfuryl acrylate, glycidyl acrylate, acrylic acid, methacrylic acid, itaconic acid, glycidyl methacrylate. Basic monomers such as dimethylaminoethyl acrylate and dimethylaminoethyl methacrylate can also be used provided that sufficient amounts of acidic deblocking agents are used.

Particularly preferred polymerizable components are mixtures of $C_1$-$C_4$ alkyl acrylates (e.g., methyl, ethyl, propyl, and butyl acrylate) and $C_1$-$C_4$-alkyl methacrylates (e.g., methyl methacrylate, ethyl methacrylate, and the like), tetrahydrofurfuryl methacrylate and tetrahydrofurfuryl acrylate, including mixtures of the preferred polymerizable components. The polymerizable compositions according to the invention may broadly comprise, based on the total weight of the acrylic adhesive composition, about 10 to about 80 wt. % (more preferably about 30 to about 70 wt. %) of the alkyl methacrylate, and about 0 to about 50 wt. % (more preferably about 2 to about 20 wt. %) of the alkyl acrylate.

U.S. Pat. No. 5,641,834 relates to a composition that includes an olefinic-terminated polyalkadiene that includes carboxy ester linking groups and at least one nascent secondary hydroxyl group that is capped with a monoisocyanate. The composition also includes a free radical-polymerizable monomer such as an olefinic monomer and, optionally, a second polymeric material. In a preferred embodiment the composition is an adhesive that also includes a phosphorus-containing compound and an ambient temperature-active redox catalyst system.

More specifically, the composition relates to (i) at least one free radical-polymerizable monomer; (ii) at least one first polymer selected from the group consisting of (a) a polymer A having a structure represented by

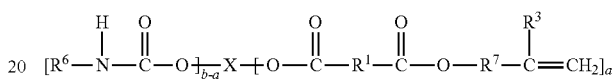

wherein X is a polyalkadiene residue, a averages from about 1.2 to about 2.6, preferably from about 1.6 to about 2.4, per polymer molecule, provided a is ≤b, b is at least 1.2, preferably about 1.2 to about 3, more preferably about 1.6 to about 2.4, per polymer molecule, $R^1$ is a divalent radical that includes at least two carbon atoms and is selected from the group consisting of saturated alkylene, substituted saturated alkylene, arylene, and saturated heterocyclic, $R^6$ is phenyl, napthyl, an alkyl group having from 1 to about 24 carbon atoms, substituted phenyl, substituted napthyl, phenylalkyl or napthylalkyl, $R^7$ has the structure

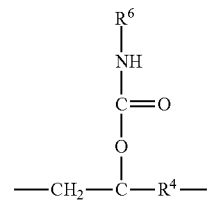

wherein $R^4$ is a divalent radical selected from the group consisting of alkylene, alkylene ester, arylene and alkylene ether, and $R^3$ is hydrogen, an alkyl group of 1 to about 4 carbon atoms, —CH=$CH_2$, or —$R^5$—CH=$CH_2$ wherein $R^5$ is an alkylene radical having 1 to about 4 carbon atoms; and (b) a polymer B having a structure represented by the formula

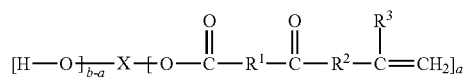

wherein X is a polyalkadiene residue, a averages from about 1.2 to about 2.6, preferably about 1.6 to about 2.4, per polymer molecule, provided a is ≤b, b is at least 1.2, preferably about 1.2 to about 3, more preferably about 1.6 to about 2.4, per polymer molecule, $R^1$ is a divalent radical that includes at least two carbon atoms and is selected from the group consisting of saturated alkylene, substituted saturated alkylene, arylene, and saturated heterocyclic, $R^2$ has the structure

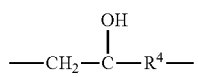

wherein $R^4$ is a divalent radical selected from the group consisting of alkylene, alkylene ester, arylene and alkylene ether, and $R^3$ is hydrogen, an alkyl group of 1 to 4 carbon atoms, —CH=CH$_2$ or —R$^5$—CH=CH$_2$ wherein $R^5$ is an alkylene radical having 1 to about 4 carbon atoms; and (iii) optionally, at least one second polymeric material selected from the group consisting of poly(acrylic) ester, poly(methacrylic) ester, poly(urethane), poly(amide), polyester, poly(oxazoline), poly(styrenic), and poly(carbonate).

U.S. Pat. No. 5,859,160 relates to a free radical curable composition that includes a free radical curable and a vinyl aromatic compound that is chemically different than the free radical curable component, wherein the vinyl aromatic compound is present in an amount sufficient to decelerate the cure rate of the free radical composition without adversely effecting completion of cure and the properties of the curable composition after it has cured. The composition is particularly useful as a two part adhesive that includes a free radical catalyst system and a diene elastomer.

The vinyl aromatic compound can be used in any curable composition that also includes a polymerizable component such as an ethylenically unsaturated compound. It is particularly useful in free radical polymerizable or curable compositions, such as described in U.S. Pat. Nos. 2,981,650; 3,321,351; 3,890,407; 4,223,115; 4,293,665; 4,467,071; 4,452,944; 4,536,546; 4,769,419 and 5,206,288, all incorporated herein by reference. Such free radical polymerizable compositions include a polymerizable component that includes at least one free radical polymerizable ethylenically unsaturated monomer characterized by the presence of a —C=C— group, polymer derived from such monomer or mixtures of monomer and polymer. It should be recognized that the ethylenically unsaturated compound of the polymerizable component is chemically different than the vinyl aromatic compound cure rate-decelerator of the invention.

(Meth)acrylic-based monomers and/or polymers derived from (meth)acrylic-based monomers are particularly useful as at least part of the polymerizable component. As used herein, (meth)acrylic-based monomer means acrylic acid, methacrylic acid or an amide, ester, salt or nitrile thereof. Representative (meth)acrylic-based monomers include, but are not limited to, methyl methacrylate, ethyl methacrylate, butyl methacrylate, methyl acrylate, butyl acrylate, cyclohexyl acrylate, hexyl acrylate, 2-ethylhexyl acrylate, lauryl acrylate, ethyl acrylate, diethylene glycol dimethacrylate, dicyclopentadienyloxyethyl methacrylate, 2-ethylhexyl methacrylate, hexyl methacrylate, cyclohexyl methacrylate, lauryl methacrylate, tetrahydrofuryl methacrylate, methacrylic acid, acrylic acid, acrylonitrile, methacrylonitrile, glycidyl methacrylate, cyanoacrylate, acrylamide and methacrylamide.

U.S. Pat. No. 5,932,638 relates to adhesive compositions which include free radical polymerizable compounds and a redox catalyst system to accelerate polymerization thereof. The redox catalyst includes an aniline derivative substituted in the para position by halogen as an accelerator. The use of para-halogenated aniline derivatives as an accelerator in the cure of free radical polymerizable compounds results in good bond strength and greatly improved surface cure of the adhesive composition.

The reducing agents of the invention include a variety of free radical polymerizable or curable compositions, such as described in U.S. Pat. Nos. 2,981,650; 3,321,351; 4,223,115; 4,293,665; 4,467,071; 4,452,944; and 4,769,419, the entire disclosure of each of which is hereby incorporated by reference. The compositions of the invention include at least one free radical polymerizable compound. Free radical polymerizable compounds that are useful in the invention include olefinic monomers characterized by the presence of a —C=C— group, for example, an olefinically unsaturated monomer selected from the group consisting of substituted and unsubstituted acrylic acid, and their amides, esters, salts and corresponding nitriles, as well as substituted and unsubstituted styrenes, and the like. Representative monomers include, but are not limited to, methyl methacrylate, ethyl methacrylate, butyl methacrylate, methyl acrylate, butyl acrylate, cyclohexyl acrylate, hexyl acrylate, 2-ethylhexyl acrylate, lauryl acrylate, ethyl acrylate, diethylene glycol dimethacrylate, dicyclopentadienyloxyethyl methacrylate, 2-ethyl hexyl methacrylate, hexyl methacrylate, cyclo hexyl methacrylate, lauryl methacrylate, tetrahydrofuryl methacrylate, methacrylic acid, acrylic acid, acrylonitrile, methacrylonitrile, styrene, vinyl styrene, vinyl acetate, chlorostyrene, glycidyl methacrylate, itaconic acid, acrylamide, methacrylamide, vinylidene chloride, 2,3-dichloro-1,3-butadiene, 2-chloro-1,3-butadiene, methylstyrene, p-tert-butyl styrene, esters of fumaric and maleic acid which are capable of free radical polymerization, and mixtures thereof. Currently preferred monomers include methyl methacrylate and styrene. The compositions of the invention typically include at least one free radical polymerizable compound in an amount from about 10 to about 90, preferably about 20 to about 70, weight percent based on the total weight of the composition.

U.S. Pat. No. 6,225,408 relates to an adhesive composition including as principal components: (a) about 10 to about 90% by weight of at least one free radical-polymerizable monomer, (b) about 0 to about 20% by weight of an adhesion promoter, (c) about 10 to about 80% by weight of a primary low molecular weight toughener (or toughening agent) with a weight average molecular weight ($M_w$) less than about 18,000 or a number average molecular number ($M_n$) less than about 10,000 and; (d) about 1 to about 15% by weight of an auxiliary high molecular weight toughener (or toughening agent) with a $M_w$ greater than about 18,000 or a $M_n$ greater than about 10,000 based on the total weight of components (a)-(d).

The invention includes about 10-90% by weight of the principal components of at least one free radical-polymerizable monomer. Free radical-polymerizable monomers in accordance with the invention are olefinic monomers that are characterized by the presence of a —C=C— group. Representative olefinic monomers include esters of (meth)acrylic acid such as methyl methacrylate, ethyl methacrylate, butyl methacrylate, methyl acrylate, butyl acrylate, cyclohexyl acrylate, hexyl acrylate, 2-ethylhexyl acrylate, lauryl acrylate, ethyl acrylate, diethylene glycol dimethacrylate, dicyclopentadienyloxyethyl methacrylate, cyclohexyl methacrylate, lauryl methacrylate, glycidyl methacrylate and tetrahydrofurfuryl methacrylate; methacrylic acid; acrylic acid; substituted (meth)acrylic acids such as itaconic acid, acrylonitrile, methacrylonitrile, acrylamide and methacrylamide; styrene; substituted styrenes such as vinyl styrene, chlorostyrene, methyl styrene and n-butyl styrene; vinyl acetate; vinylidene chloride; and butadienes such as 2,3-dichloro-1,3-butadiene and 2-chloro-1,3-butadiene. Other olefinic monomers include maleate esters; fumarate esters; and styrenic compounds such as styrene, chlorostyrene, methylstyrene, butylstyrene and vinyl styrene. Tetrahydrofurfuryl methacrylate (THFMA), methacrylic acid and methyl methacrylate are most preferred.

U.S. Pat. No. 6,559,257 relates to an adhesive that includes a free radical-polymerizable monomer component that includes at least a reaction product of a (hydroxy)acrylate with an anhydride but is substantially free of methyl methacrylate or methacrylic acid.

The (hydroxy) acrylate compound utilized to prepare the reaction product included in the monomer component of the invention can be any acrylate compound characterized by the presence of a hydroxy group. Examples of suitable hydroxy-functional acrylate compounds include 2-hydroxyethyl acrylate, 2-hydroxyethyl methacrylate, 2-hydroxypropyl acrylate, 2-hydroxypropyl methacrylate, 2-hydroxybutyl acrylate, 2-hydroxybutyl methacrylate, 3-hydroxypropyl acrylate, 4-hydroxybutyl acrylate, 3-hydroxypentyl acrylate, 6-hydroxynonyl acrylate, 3-hydroxypropyl methacrylate, 2-hydroxypentyl methacrylate, 5-hydroxypentyl methacrylate, 7-hydroxyheptyl methacrylate, 5-hydroxydecyl methacrylate, N-hydroxymethyl acrylamide, N-hydroxymethyl methacrylamide, diethylene glycol monoacrylate, diethylene glycol monomethacrylate, glycerin dimethacrylate, tri-methylol propane dimethacrylate, alkoxylated hydroxyethyl acrylate, trimethylolpropane diacrylate, alkoxylated trimethylolpropane diacrylate, reaction products of polyether glycols of acrylic or methacrylic acid and the like.

U.S. Pat. No. 6,660,805 relates to an epoxy-modified, two-part acrylic structural adhesives. These adhesives are not inhibited by oxygen. Representative embodiments include 2-part acrylic structural adhesives comprising, in a first package from about 10 to about 90 percent by weight of at least one methacrylate selected from $C_3$-$C_{10}$ alkyl monosubstituted-, $C_1$-$C_6$ alkyl disubstituted-, $C_1$-$C_4$ alkyl tri-substituted, and $C_1$-$C_4$ alkyl tetra-substituted cyclohexyl methacrylate. The ring substituents are preferably in the 3, 4, and/or 5 ring position, and linear or branched $C_4$-$C_{10}$ branched alkyl methacrylates; from about 10 to about 80 percent by weight of a toughener, and an adhesion promoter; and in a second package, a bonding activator, and optional epoxy resin.

U.S. Pat. No. 5,096,962 relates to a one-component adhesive for metal surfaces such as iron, zinc, copper, cadmium and their alloys that will cure upon contact with the metal surface. The adhesive composition includes an olefinically unsaturated monomer; an acidic compound; a sulfonyl-containing compound; and a compound containing a transition metal. The adhesive composition may also optionally contain additional polymeric materials and will cure rapidly upon contact with a metal surface to form an adhesive bond between metal surfaces. The adhesive composition avoids the use of halide-containing compounds which can be undesirable in certain applications.

In particular, the single-package adhesive compositions of this invention comprise, in admixture, (A) at least one olefincially unsaturated monomer; (B) an acidic compound having at least one organic or inorganic acid group; (C) at least one sulfonyl-containing compound selected from the group consisting of certain sulfonyl-sulfur, sulfonyl-phosphorus and sulfonyl-silicon compounds hereinafter defined; and (D) at least one organic or inorganic compound containing at least one reducible transition metal, said metal having its valence electrons in a "d" subshell, said metal being selected from the elements of classes Ib, IIb, IIIb, IVb, V, VIb, VIIb, or VIII on the periodic chart of the elements; with copper, zinc, iron, cobalt and nickel being preferred, with copper being especially preferred, said metal being most preferably in its highest oxidation state; wherein the amount of said olefinically unsaturated monomer is in the range from about 10 to about 90, preferably about 17 to about 87, percent by weight; the amount of said acidic compound is in the range from about 0.05 to about 20, preferably about 0.1 to about 15, percent by weight; the amount of said sulfonyl-containing compound is in the range from about 0.05 to about 5, preferably about 0.5 to about 2, percent by weight; and the amount of said transition metal compound is in the range from about 0.05 to about 5, preferably about 0.5 to about 2.5, percent by weight; said weight percents being based on the total weight of the adhesive composition.

As noted in the above incorporated by reference patents, many different types of acrylic adhesion compositions can be utilized in the present invention. Generally, such acrylic adhesion compositions comprise at least two parts or components, that is a) one or more ethylenically unsaturated compounds formulated with a reducing agent coreactive with, b) an oxidizing agent capable of generating free radicals therewith. Another acrylic adhesion composition generally comprises one or more ethylenically unsaturated compounds formulated with an initiator component activated on contact with a suitable metal substrate or substrate primed with a coreactive agent. In addition to these components, the acrylic adhesion composition can contain optionally one or more of the following: fillers, rubber tougheners, coloring agents, speed control agents, oxygen barrier compounds, redox catalysts, and the like.

Additional Example Formulations

The carboxylic acid containing phosphonic acid adhesion promoters of the present invention such as set forth in Schemes II, III, and IV, can be utilized in an amount of from about 0.1 to about 20 parts by weight, desirably from about 0.4 to about 3.0 parts by weight, and preferably from about 0.8 to about 2.0 parts by weight based upon the total of 100 parts by weight of an adhesive composition that preferably is an acrylic adhesive composition.

The formulation was prepared again using two above-noted different PBTA-based adhesion promoters as well as controls and used to bond oiled steel coupons of the same type as above. The oil used was Ferrocote 61 AUS applied at 0.31±0.02 g/cm². The T-peel values are listed in Table 3 below.

TABLE 3

| Formulation | Average Maximum Load (lbf) | Average Avg LD/W (lbs/in) | Failure Mode* |
|---|---|---|---|
| Control (no adhesion promoter) | 133 ± 9 (5) | 1,600 ± 200 (5) | 100 ± 0% (5) ADH |
| Control (LORD HEMA-phosphate) | 320 ± 30 (5) | 9,300 ± 400 (5) | 60 ± 30% (5) COH/TLC |
| PBTA-based (Example A) | 360 ± 10 (5) | 9,600 ± 200 (4) | 70 ± 20% (4) COH/TLC |
| PBTA-based (Example B) | 360 ± 40 (5) | 7,000 ± 500 (5) | 82 ± 8% (5) ADH/TLC |

*ADH = adhesive; COH = cohesive; TLC = thin layer cohesive

As apparent from Table 3, the Example A adhesion promoter gave much better results than either of the Controls. Adhesion promoter Example B was much better than the no adhesion promoter Control but was not as good as the Lord Control adhesion promoter or the Example A adhesion promoter. The reason for the poorer performance of the Example B formulation relative to Example A probably arises from the poorer solubility of the HEMA adduct of Formula 1a or 1b species that forms when azeotropic dehydration is used in the second step resulting in a lower overall level of adhesion promoting species in this trial.

The same batches of adhesive were also used to assemble lap shear coupons covered with the same oil. The displacement, maximum strain, and failure mode are summarized in Table 4.

TABLE 4

| Formulation | Average Maximum Displacement (m) | Average Maximum Strain (N) | Failure Mode* |
|---|---|---|---|
| Control (no adhesion promoter) | 0.001 ± 0.000 (5) | 2,200 ± 400 (5) | 100 ± 0% (5) ADH |
| Control (LORD HEMA-phosphate) | 0.012 ± 0.0.002 (5) | 9,800 ± 400 (5) | 99 ± 2% (5) ADH/TLC |
| PBTA-based (Example A) | 0.009 ± 0.003 (5) | 8,900 ± 900 (5) | 70 ± 30% (5) ADH/TLC |
| PBTA-based (Example B) | 0.007 ± 0.002 (5) | 8,700 ± 400 (5) | 92 ± 4% (5) ADH/TLC |

*ADH = adhesive; COH = cohesive; TLC = thin layer cohesive

Once again Examples A and B gave large improved results over the Control containing no adhesion promoter and yielded lower amounts of adhesive failure than the LORD Control.

In accordance with the patent statutes, the best mode and preferred embodiments have been set forth, the scope of the invention is not limited thereto, but rather by the scope of the attached claims.

What is claimed is:

1. A carboxylic acid containing phosphonic acid adhesion promoter comprising:
   a compound of the formula

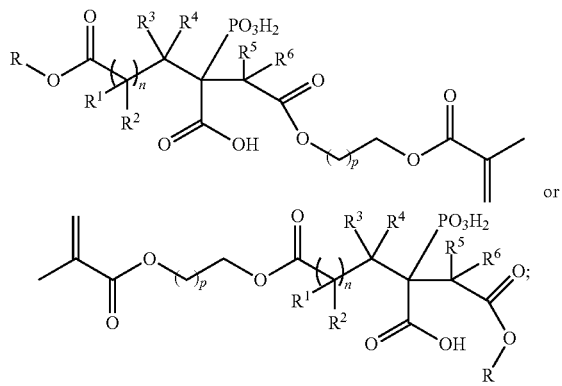

where R, independently, is an alkyl having from 1 to about 18 carbon atoms;
$R^1$, independently, is H, or an alkyl comprising from 1 to about 6 carbon atoms,
$R^2$, independently, is H, or an alkyl comprising from 1 to about 6 carbon atoms,
$R^3$, independently, is H, or an alkyl comprising from 1 to about 6 carbon atoms,
$R^4$, independently, is H, or an alkyl comprising from 1 to about 6 carbon atoms,
$R^5$, independently, is H, or an alkyl comprising from 1 to about 6 carbon atoms, and
$R^6$, independently, is H, or an alkyl comprising from 1 to about 6 carbon atoms; and
wherein n, independently, is 0 or 1, and p, independently, is from about 1 to about 35.

2. The phosphonic acid adhesion promoter of claim 1,
wherein R is an alkyl having from 1 to about 18 carbon atoms,
$R^1$, independently, is H, or an alkyl comprising from 1 to about 2 carbon atoms,
$R^2$, independently, is H, or an alkyl comprising from 1 to about 2 carbon atoms,
$R^3$, independently, is H, or an alkyl comprising from 1 to about 2 carbon atoms,
$R^4$, independently, is H, or an alkyl comprising from 1 to about 2 carbon atoms,
$R^5$, independently, is H, or an alkyl comprising from 1 to about 2 carbon atoms, and
$R^6$, independently, is H, or an alkyl comprising from 1 to about 2 carbon atoms; and
wherein p is from about 1 to about 9.

3. The phosphonic acid adhesion promoter of claim 2,
wherein R is an alkyl having from 1 to about 4 carbon atoms;
$R^1$ is H,
$R^2$ is H,
$R^3$ is H,
$R^4$ is H,
$R^5$ is H, and
$R^6$ is H; and
wherein p is about 1 to 5.

4. An adhesion composition comprising an acrylic adhesive composition and from about 0.4 to about 3.0 parts by weight of the phosphonic acid adhesion promoter of claim 3 based upon 100 parts by weight of said acrylic adhesion composition.

5. The adhesion composition of claim 4, wherein said acrylic adhesion composition comprises at least two parts: a) one or more ethylenically unsaturated compounds formulated with a reducing agent, and b) an oxidizing agent, wherein the reducing agent is coreactive with the oxidizing agent to generate free radicals.

6. The adhesion composition of claim 4, wherein said acrylic adhesion composition comprises one or more ethylenically unsaturated compounds formulated with an initiator component activated on contact with a metal substrate or a substrate primed with a coreactive agent.

7. An adhesion composition comprising an acrylic adhesive composition and from about 0.1 to about 20 parts by weight of the phosphonic acid adhesion promoter of claim 2 based upon 100 parts by weight of said acrylic adhesion composition.

8. The adhesion composition of claim 7, wherein said acrylic adhesive composition comprises at least two parts: a) one or more ethylenically unsaturated compounds formulated with a reducing agent, and b) an oxidizing agent, wherein the reducing agent is coreactive with the oxidizing agent to generate free radicals.

9. The adhesion composition of claim 7, wherein said acrylic adhesive composition comprises one or more ethylenically unsaturated compounds formulated with an initiator component activated on contact with a metal substrate or a substrate primed with a coreactive agent.

10. The phosphonic acid adhesion promoter of claim 1, wherein said adhesion promoter is

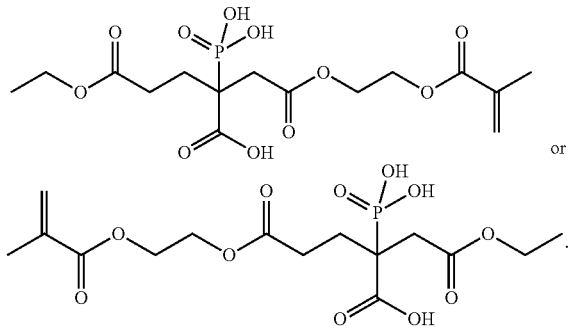

11. An adhesion composition comprising an acrylic adhesive composition and from about 0.8 to about 2.0 parts by weight of the phosphonic acid adhesion promoter of claim 10 based upon 100 parts by weight of said acrylic adhesion composition.

12. The adhesive composition of claim 11, wherein the acrylic adhesive composition comprises at least two parts: a) one or more ethylenically unsaturated compounds formulated with a reducing agent, b) an oxidizing agent, wherein the reducing agent is coreactive with the oxidizing agent to generate free radicals.

13. The adhesive composition of claim 11, wherein the acrylic adhesive composition comprises one or more ethylenically unsaturated compounds formulated with an initiator component activated on contact with a metal substrate or a substrate primed with a coreactive agent.

14. A laminate comprising a metal substrate bonded to a non-metallic substrate by an acrylic adhesive composition comprising the carboxylic acid containing phosphonic acid adhesion promoter of claim 10.

15. The laminate of claim 14, wherein said metallic substrate comprises steel, stainless steel, aluminum, galvanized steel, phosphated steel, copper, brass, bronze, lead, nickel, or any combination thereof; and wherein said non-metallic substrate comprises a rubber or plastic substrate and said rubber comprises natural rubber, polychloroprene rubber, styrenebutadiene rubber, nitrile rubber, ethylene/-propylene copolymer rubber (EPM), ethylene/-propylene/diene terpolymer rubber (EPDM), butyl rubber, polyurethane rubber, and any combination thereof; and wherein said plastic comprises polyamide, polyester, aramide, polyurethane, or any combination thereof.

16. A laminate of claim 15, wherein said acrylic adhesive composition comprises at least two parts: a) one or more ethylenically unsaturated compounds formulated with a reducing agent, and b) an oxidizing agent, wherein the reducing agent is coreactive with the oxidizing agent to generate free radicals.

17. An adhesion composition comprising the phosphonic acid adhesion promoter of claim 1 in an acrylic adhesive composition.

18. The adhesion composition of claim 17, wherein said acrylic adhesion composition comprises at least two parts: a) one or more ethylenically unsaturated compounds formulated with a reducing agent, and b) an oxidizing agent, wherein the reducing agent is coreactive with the ocidizing agent to generate free radicals.

19. The adhesion composition of claim 17, wherein said acrylic adhesion composition comprises one or more ethylenically unsaturated compounds formulated with an initiator component activated on contact with a metal substrate or a substrate primed with a coreactive agent.

20. A laminate comprising a metal substrate bonded to a non-metallic substrate by an acrylic adhesive composition comprising the carboxylic acid containing phosphonic acid adhesion promoter of claim 1.

21. The laminate of claim 20, wherein said metallic substrate comprises steel, stainless steel, aluminum, galvanized steel, phosphated steel, copper, brass, bronze, lead, nickel, or any combination thereof; and wherein said non-metallic substrate comprises a rubber or plastic substrate and said rubber comprises natural rubber, polychloroprene rubber, styrenebutadiene rubber, nitrile rubber, ethylene/-propylene copolymer rubber (EPM), ethylene/-propylene/diene terpolymer rubber (EPDM), butyl rubber, polyurethane rubber, and any combination thereof; and wherein said plastic comprises polyamide, polyester, aramide, polyurethane, or any combination thereof.

22. A laminate of claim 20, wherein said acrylic adhesive composition comprises at least two parts: a) one or more ethylenically unsaturated compounds formulated with a reducing agent, and b) an oxidizing agent, wherein the reducing agent is coreactive with the oxidizing agent to generate free radicals.

* * * * *